United States Patent [19]

Hsu et al.

[11] 4,442,036
[45] Apr. 10, 1984

[54] PROCESS FOR OXIDIZING PHENOL TO BENZOQUINONE

[75] Inventors: Chao-Yang Hsu, Media; James E. Lyons, Wallingford, both of Pa.

[73] Assignee: Sun Tech, Inc., Philadelphia, Pa.

[21] Appl. No.: 470,694

[22] Filed: Feb. 28, 1983

[51] Int. Cl.³ .............................................. C07C 49/64
[52] U.S. Cl. ................................................. 260/396 R
[58] Field of Search .................................... 260/396 R

[56] References Cited

U.S. PATENT DOCUMENTS 3,870,731  3/1975  Hutchings ........................ 260/390 R
3,987,068  10/1976 Reilly ............................... 260/396 R
4,208,339  6/1980  Costantini et al. .............. 260/396 R
4,235,790  11/1980 Müller et al. .................... 260/396 R
4,257,968  3/1981  Reilly ............................... 260/396 R

FOREIGN PATENT DOCUMENTS 15221  9/1980  European Pat. Off. ........ 260/396 R

Primary Examiner—Natalie Trousof
Assistant Examiner—Raymond Covington
Attorney, Agent, or Firm—J. Edward Hess; Donald R. Johnson; Patrick C. Baker

[57] ABSTRACT

Phenol is oxidized to benzoquinone with a bivalent copper catalyst using a vicinal dialkoxy alkane or cycloalkane as promoter, whereby improved conversion and/or selectivity is obtained.

10 Claims, No Drawings

PROCESS FOR OXIDIZING PHENOL TO BENZOQUINONE

BACKGROUND OF THE INVENTION

It is known in the art to oxidize phenol to benzoquinone, e.g., para-benzoquinone with oxygen in the presence of a copper ion catalyst and such a process is disclosed in U.S. Pat. No. 3,987,068. In that patent the oxidation is carried out in a nitrile solvent using a complex formed from the copper catalyst and the solvent and the operating conditions are said to be at temperatures of from about 0° to 100° C. and a partial pressure of oxygen of from about 7 to 200 (preferably 14 to 100) atmospheres. As pointed out in U.S. Pat. No. 3,987,068, yield of quinone product increases with increased partial pressure of oxygen and it appears from the data therein that partial pressures of oxygen above about 100 atmospheres are required in order to achieve conversions of phenol to p-benzoquinone on the order of about 75%. Such pressures are too high to be useful in an economical commercial process because they require special equipment of high capital cost.

U.S. Pat. No. 3,870,731 relates to the oxidation of phenols to benzoquinones in the presence of copper salts as catalyts where the catalyst is promoted with thiocyanate, cyanate, cyanide and halogen ions. In such reactions a solvent such as water is disclosed and other polar solvents soluble or miscible with water may be used. Such solvents are exemplified as certain amides, alcohols, and sulfoxides.

U.S. Pat. No. 4,208,339 discloses a process for the preparation of p-benzoquinone by oxidation of phenol in the presence of cuprous or cupric ions in the presence of a metal in the metallic form in a nitrile, amide, alcohol or sulfoxide solvent. Reaction rate is said to be increased by including an alkali metal or alkaline earth metal halide.

In South African patent publication No. 78/5012 on the oxidation of phenol to p-benzoquinone with a cuprous or cupric catalyst, the presence of a reducing agent for cupric ion to cuprous ions is said to give improved yield and/or improved conversion. Such reducing agents are exemplified by diphenol, a substituted alkylphenol, an aliphatic aldehyde, an aliphatic ketone of 3 to 6 carbon atoms, or an aliphatic or cycloaliphatic olefin or diolefin.

SUMMARY OF THE INVENTION

It has now been found that the copper catalyzed process for oxidation of phenol to benzoquinone, especially p-benzoquinone, can be significantly improved so as to enable operation at lower, commercially useful pressures and still achieve an improved conversion and/or improved selectivity to product. In accord with the invention, such objectives are achieved by conducting the oxidation of phenol in the presence of a divalent copper ion catalyst (e.g. $Cu^{++}$) which is promoted with a vicinal dialkoxy alkane or cycloalkane, of which dimethyoxypropane and dimethoxycyclohexane are representative.

DETAILED DESCRIPTION

In carrying out the process of the invention conventional temperature conditions, solvent systems and divalent (i.e., cupric) copper catalyst may be used. Thus, a temperature of from about 20° to about 100° C. (preferably about 50° to 75° C.) and a substantially inert, polar organic solvent, are usually employed. Suitable solvents include nitriles such as acetonitrile and propionitrile; aliphatic ketones such as acetone, methylethyl ketone, methylisopropyl ketone and mesityl oxide; $C_1$-$C_4$ aliphatic alcohols such as methanol and ethanol; an amide such dimethyl formamide; secondary amines such as diethylamine; and sulfoxides. Nitriles are preferred, particularly the lower alkyl (e.g., $C_1$-$C_8$) nitriles. The copper catalyst preferably will be a copper II halide, preferably chloride, nitrate or a mixture of such salts. Certain other copper II salts, such as acetates, sulfates, benzoates, carbonates, phosphates and bisulfates have been found to be ineffective catalysts for the reaction.

The promoter for the process of this invention is a vicinal dialkoxy alkane or cycloalkane, also known as ketals, of the structure

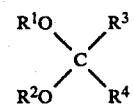

where $R^1$ and $R^2$ independently are lower alkyl (e.g., $C_1$-$C_8$), $R^3$ and $R^4$ independently are hydrogen or lower alkyl (e.g., $c_1$-$C_8$), and $R^3$ together with $R^4$ and the carbon atom to which they are bonded, when $R^3$ and $R^4$ are alkyl, may form a cycloalkyl (e.g., $C_3$-$C_8$) group, e.g., cyclopropyl, cyclohexyl or cycloheptyl. The R groups may be straight chain or branched. The promoters thus may contain 3 to about 20 carbon atoms or more, but more usually contain up to about 12 carbon atoms. Representative promoters include methylal, 2,2-dimethoxy- and 2,2-diethoxypropane, 2,2-dimethoxy- and 2,2-diethoxybutane, 1,1-dimethoxy- and 1,1-diethoxycyclohexane, and the like. Mixtures of two or more of the promoters may be used.

The reaction can be carried out at moderate pressures, generally between about 100 and about 500 psig partial pressure of molecular oxygen, preferably between about 200 and 400 psig. Mixtures of oxygen and nitrogen, air alone, or oxygen alone may be used, but preferably mixtures of oxygen and nitrogen such as air will be employed as the oxygenating medium. The reaction system will be anhydrous initially, but since the oxidation of one mole of phenol to benzoquinone is known to generate one mole of water, some water will be formed during the reaction. The water can be removed as formed by conventional means or can be left in the reaction mixture to further promote the reaction.

In order to further illustrate the invention, the following example of a series of reaction runs is given.

EXAMPLE

A solution of 16 mmole of phenol in 5 ml. of acetonitrile containing 0.55 mmole of copper catalyst and the designated quantity of 2,2-dimethoxypropane as promoter is agitated in a magnetically stirred mini-autoclave under an initial total pressure of 750 psig and is oxidized over a three-hour period with a mixture of 40% (vol.) oxygen and 60% nitrogen. For comparison purposes a monovalent copper catalyst (CuCl) is included in several of the runs. The reaction parameters and results which are obtained are shown in the following Table I.

TABLE 1
EFFECT OF 2,2-DIMETHOXYPROPANE (DMP) ON THE COPPER CATALYZED OXIDATION OF PHENOL TO p-BENZOQUINONE (PBQ)

| Cat. | Mmoles Cat. | Promoter | Mmoles Promoter | Mmoles Phenol | Temp. | Time (Min.) | Select PBQ (%) | Conv. (%) | Yield PBQ (%) |
|---|---|---|---|---|---|---|---|---|---|
| CuCl$_2$ | 0.55 | — | — | 3.51 | 65 | 180 | 42 | 85 | 36 |
| CuCl$_2$ | 0.55 | — | — | 8.00 | 65 | 180 | 43 | 70 | 30 |
| CuCl$_2$ | 0.55 | DMP | 5 | 7.46 | 65 | 180 | 62 | 93 | 58 |
| CuCl$_2$ | 0.55 | DMP | 5 | 8.22 | 65 | 180 | 60 | 90 | 54 |
| CuCl | 0.55 | — | — | 16.00 | 65 | 180 | 61 | 47 | 29 |
| CuCl | 0.55 | DMP | 5 | 16.00 | 65 | 180 | 69 | 48 | 33 |

Table I shows that the CuCl$_2$-catalyzed oxidation of phenol gives only 42% selectivity to p-benzoquinone at 85% conversion when reaction is carried out at 65° C. for 180 minutes at 750 psig of 40% O$_2$/60% N$_2$. Under the same conditions in the presence of about 10 weight percent dimethoxypropane, the selectivity to p-benzoquinone exceeds 60% and conversion exceeds 90%. It will also be noted that the DMP has little effect with the monovalent copper catalyst (CuCl).

We claim:

1. In the process of oxidizing phenol to benzoquinone in a polar organic solvent with a bivalent copper catalyst, the improvement which comprises obtaining increased selectivity and/or conversion by promoting the catalyst with a vicinal dialkoxy alkane or cycloalkane.

2. The process of claim 1 wherein the catalyst is cupric chloride.

3. The process of claim 1 wherein the catalyst is cupric nitrate.

4. The process of claim 1 wherein the alkoxy groups of the promoter are lower alkoxy.

5. The process of claim 1 wherein the promoter has the formula:

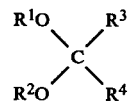

wherein R$^1$ and R$^2$ independently are lower alkyl, R$^3$ and R$^4$ independently are lower alkyl or hydrogen, and R$^3$ and R$^4$ together with the carbon atom to which they are bonded, when R$^3$ and R$^4$ are alkyl, may form a cycloalkyl group.

6. The process of claim 1 wherein the promoter is methylal, 2,2-dimethoxypropane, 2,2-diethoxypropane, 2,2-dimethoxybutane, 2,2-diethoxybutane, 1,1-dimethoxycyclohexane or 1,1-diethoxycyclohexane.

7. The process of claim 1 wherein the promoter is 2,2-dimethoxypropane, the catalyst is cupric chloride, and the solvent is a nitrile.

8. The process of claim 1 wherein the promoter is 2,2-dimethoxypropane, the catalyst is cupric nitrate, and the solvent is a nitrile.

9. The process of claim 7 wherein the solvent is acetonitrile.

10. The process of claim 8 wherein the solvent is acetonitrile.

* * * * *